United States Patent [19]
Jakubowicz et al.

[11] Patent Number: 5,244,633
[45] Date of Patent: Sep. 14, 1993

[54] ANALYZER INCUBATOR WITH PLURAL INDEPENDENTLY DRIVEN RINGS SUPPORTING CUVETTES

[75] Inventors: Raymond F. Jakubowicz; Johannes J. Porte; James E. Robinson, all of Webster, N.Y.

[73] Assignee: Eastman Kodak Company, Rochester, N.Y.

[21] Appl. No.: 887,990

[22] Filed: May 22, 1992

[51] Int. Cl.$^5$ ............................................ G01N 35/06
[52] U.S. Cl. ..................................... 422/64; 422/63; 422/67; 422/103; 436/43; 436/47; 436/48; 435/809
[58] Field of Search ................. 422/64, 63, 67, 82.05, 422/82.12, 109, 103; 435/290, 316, 809; 436/43, 47, 48, 49, 157, 165, 172

[56] References Cited

U.S. PATENT DOCUMENTS

| | | |
|---|---|---|
| 3,728,227 | 4/1973 | Elson ........................................ 422/50 |
| 3,756,920 | 9/1973 | Kelbaugh et al. ..................... 422/52 |
| 3,758,274 | 9/1973 | Ritchie et al. ......................... 422/50 |
| 4,219,527 | 8/1980 | Tersteeg et al. ....................... 422/65 |
| 4,595,562 | 6/1986 | Liston et al. ........................... 422/65 |
| 4,699,766 | 10/1987 | Yamashita ............................. 422/64 |
| 4,834,944 | 5/1989 | Wakatake .............................. 422/64 |
| 4,906,433 | 3/1990 | Minekane .............................. 422/64 |
| 5,051,238 | 9/1991 | Umetsu et al. ........................ 422/64 |

FOREIGN PATENT DOCUMENTS

3839080 11/1988 Fed. Rep. of Germany.

Primary Examiner—James C. Housel
Assistant Examiner—Long V. Le
Attorney, Agent, or Firm—Dana M. Schmidt

[57] ABSTRACT

An incubator and an incubator method using two independently driven incubator rings each holding and transferring a liquid-containing cuvette between processing stations. At least one reagent addition station is disposed permanently adjacent each of the two rings. One advantageous result is enhanced throughput compared to having only one such ring for all reagent addition stations.

13 Claims, 11 Drawing Sheets

ANALYZER INCUBATOR WITH PLURAL INDEPENDENTLY DRIVEN RINGS SUPPORTING CUVETTES

FIELD OF THE INVENTION

This invention relates to analyzer incubators, particularly those used to incubate liquid-containing cuvettes.

BACKGROUND OF THE INVENTION

Certain immunoassays, such as thyroxine (T4) and thyroid stimulating hormone (TSH), have conventionally been done as a wet assay, that is, by using liquid reagents in a cuvette. In one such assay, the enhanced chemiluminescence system originally developed by Amersham International and sold under the tradename Amerlite, the cuvette has an antibody for the target antigen pre-adhered to the cuvette. The liquid sample is added to the cuvette, followed by at least one liquid reagent containing a labeled antibody to the antigen, and the liquid mix is incubated. Following incubation, the mix in the well is aspirated out, followed by multiple washings, to separate bound labeled antibody from unbound labeled antibody. Thereafter, at least one signal generating reagent is added in liquid form to induce enhanced chemiluminescence, which is then read.

All of these steps are time-consuming in their totality. This is handled in the Amerlite system by making the operation a batch operation—the cuvettes are given the sample and first liquid reagent, and incubated, in one apparatus, and then transferred to a different apparatus for washing. Still further, a third apparatus is used for adding the signal-generating reagent and another for reading. In that manner, a first set of cuvettes can be incubating while a second one is being washed and a third is being read, to enhance throughput.

One drawback of such a system is that the three separate stations are not one automated instrument. Other instruments are known that have a single unit to provide incubation and reading, such as is described in German OLS 3,839,080 wherein all incubation functions occur while the cuvette is on a single rotating ring 302. That is, cuvettes 301' have an antibody pre-attached to the wells, p. 9, and the liquid sample, liquid reagents, incubation, washing (station 309) and light-detection (station 325) all occur while the cuvettes are carried around the one ring. However, the provision of all the above-numbered functions in that single incubator ring creates a disadvantage—the throughput is considerably reduced since every step has to occur on the single ring. The washing step alone can take 8 seconds.

The problem, therefore, has been to create an automated analyzer for cuvettes handling liquid reagents, that automates reagent addition, incubation, washing and detection, but with a high throughput not readily provided by an incubator handling all the functions in one rotating support.

SUMMARY OF THE INVENTION

We have devised an analyzer incubator and incubation method that solve the afore-mentioned problems. More specifically, there is provided in accord with one aspect of the invention, an analyzer incubator comprising plural support rings for carrying between processing stations of the incubator, reaction cuvettes held at defined positions;

means for rotating each of the support rings independently between the stations;

means for moving at a transfer location, a reaction cuvette from one support ring to the other at an appropriate stage within the incubation; and processing stations adjacent to the rings to provide separately the functions of sample addition, first liquid reagent addition, second liquid reagent addition, cuvette washing, optional third liquid reagent addition, and detection of light emitted from the reaction cuvettes, at least the first liquid addition station being permanently disposed adjacent to at least one of the rings, while at least the second liquid reagent addition station is permanently disposed adjacent to at least another of the rings;

and temperature control means adjacent to both of the rings, so that higher throughput is achieved by separating and distributing the incubating functions onto more than one support ring.

In accord with another aspect of the invention, there is provided a method for incubating cuvettes in an analyzer, comprising the steps of a) placing a cuvette and a liquid sample in the cuvette in one of a plurality of support rings, in a defined position on the ring, b) rotating the ring and the cuvette about an axis between processing stations disposed adjacent to the ring, while incubating the contents of the cuvette, c) transferring a cuvette following partial incubation, to another of the plurality of support rings, and d) rotating the other ring and cuvettes held therein about the axis while incubating and while passing through at least one reagent-addition station.

Accordingly, it is an advantageous feature of the invention that all the incubation functions of adding liquid reagent(s) and a sample to a cuvette and washing the contents of the cuvette, all while controlling the temperature of the cuvette, can be done automatically while obtaining high throughput.

It is a related advantageous feature of the invention that the cuvette washing function of the incubation can be done independently of the incubation following first liquid reagent.

It is a further advantageous feature of the invention that the incubation functions are split up into two independently driven parts of the incubator, and transfer between the two parts is achieved quickly and efficiently.

Other advantageous features of the invention will become apparent upon reference to the following detailed Description of the Invention, when read in light of the attached drawings.

DETAILED DESCRIPTION OF THE PREFERRED EMBODIMENTS

The invention is hereinafter described in connection with the preferred embodiments of an incubator of an analyzer having plural processing stations disposed around concentrically mounted plural rings, of a preferred type that make use of a reaction cuvette and certain reagents, to treat a sample obtained from a sample supply station by aspiration. In addition, the invention is useful regardless of the number and type of processing stations of the analyzer, regardless of the type of cuvettes and reagents used, whether the rings are concentrically mounted or not, and regardless of how cuvettes, reagents and samples are supplied to the incubator, since those features are not the invention, as long as at least one reagent addition station is permanently disposed adjacent to at least each of the plural rings of the incubator to enhance throughput. As used herein, "reagent addition station" means, the location at the respective ring at which the function of reagent addition occurs. The apparatus used at such a station may, and in fact preferably does, move to other locations as well.

THE ANALYZER

Figure 1:
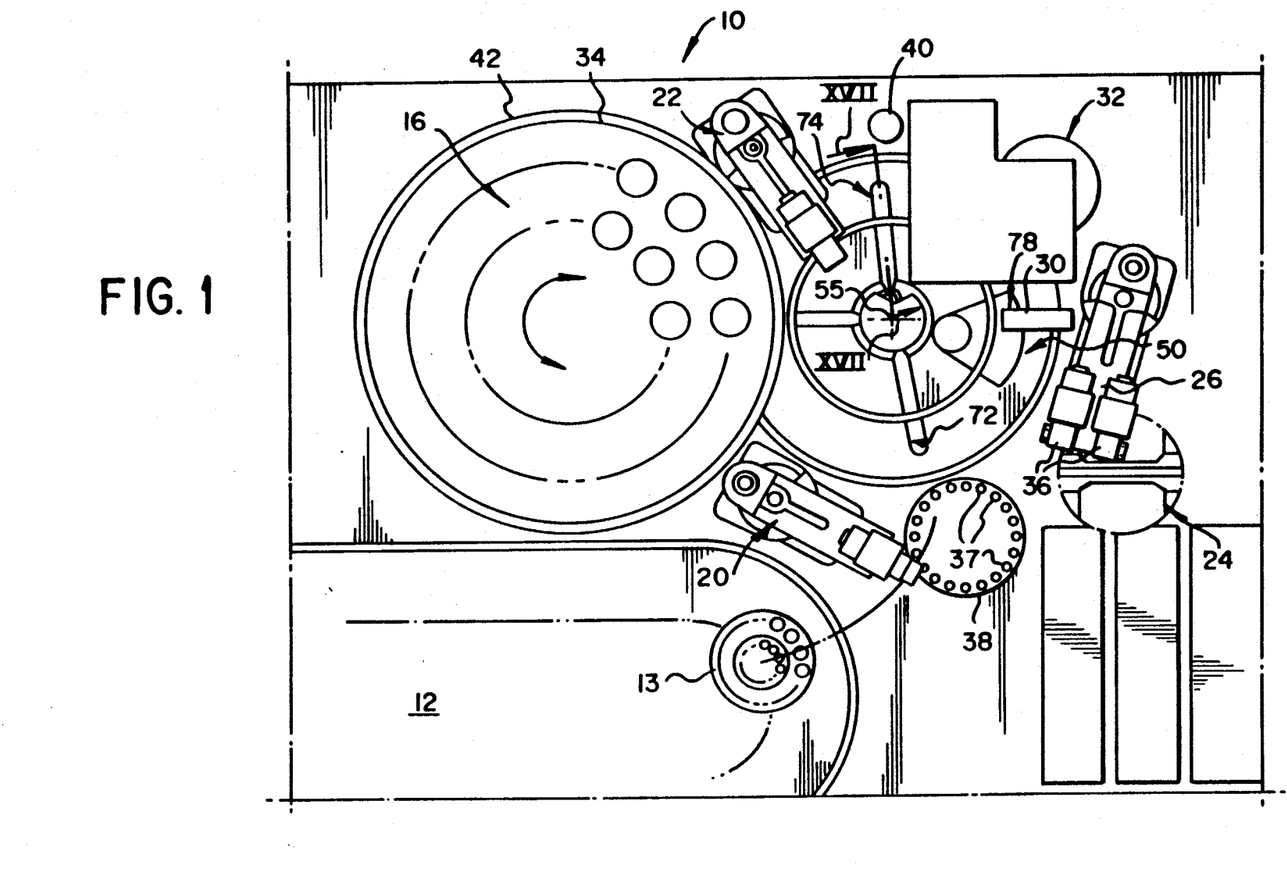
FIG. 1 is a schematic, broken away plan view of an analyzer incorporating the incubator of the invention.
Figure 2:
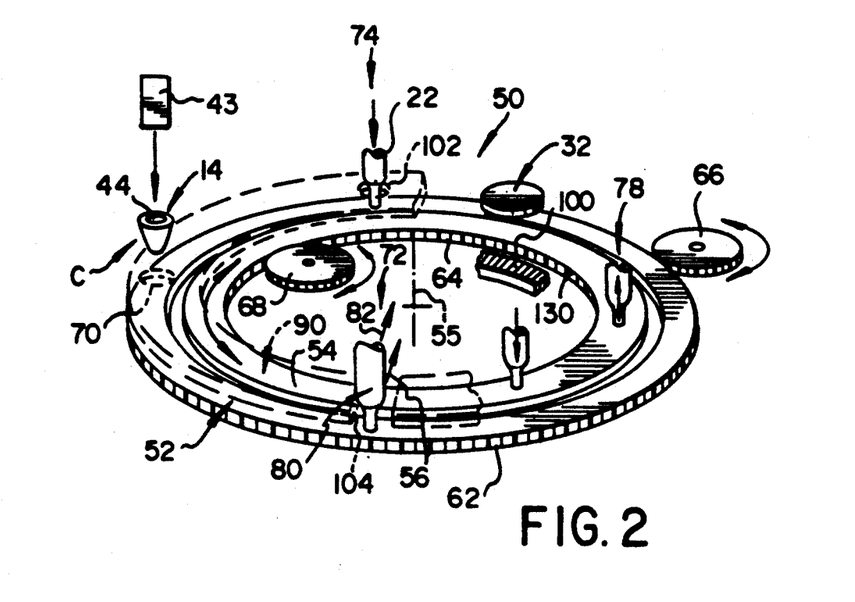
FIG. 2 is a partially schematic, fragmentary isometric view of the incubator per se and of the processing stations associated therewith.

Thus, as shown in FIG. 1, the incubator of the invention is constructed for use in an analyzer 10 comprising a sample supply station 12, a cuvette supply station 14, FIG. 2, a reagent supply station 16, FIG. 1, incubator 50, means 20 and 22 for transferring sample and reagent to a cuvette disposed in an outer ring of incubator 50, signal reagent supply station 24, means 26 for transferring signal reagent to the cuvette in an inner ring of incubator 50, cuvette wash station 30, and luminometer 32. Except for the incubator and the location of the stations for reagent addition described hereinafter, any suitable construction, including conventional devices, can be used for the sample supply station 12, cuvette supply station 14, reagent supply station 16, transfer means 20, 22 and 26, signal reagent supply station 24, wash dispenser 30, and luminometer 32. For example, the following features are considered to be conventional: supply station 12 includes a position having a device 13 therein that is aligned for sample transfer. (Useful devices 13 include those described and claimed in commonly owned, pending U.S. application Ser. No. 859,780 filed on Mar. 30, 1992 by Tomasso et al, entitled "Tray and Magnetic Conveyor".) Supply station 16 includes a rotor 34, transfer means 20, 22 and 26 are all preferably pivoting aspirators, the aspirator at transfer means 26 having dual probes 36. Transfer means 20 preferably uses disposable tips, which can be presented for pick-up on supply station 12. Additional tips 37 can be presented on turntable 38 for use by means 20 during a dilution step. On the other hand, the aspirator for transfer means 22 preferably uses a more permanent dispensing tip, which uses a wash station 40 as is conventional.

Cuvettes can be disposed for dispensing at station 14 by mounting them in, e.g., a ring 42 that moves with rotor 16, any suitable pusher 43, FIG. 2, being used to displace a cuvette from ring 42 into incubator 50 below.

Although any cuvette can be used, preferably it is a cup-like container "C", having on its inside wall surface 44 an antibody pre-attached to the wall surface. The antibody is useful in a conventional sandwich assay which produces a complex of antibody-antigen-labeled antibody for generating a chemiluminescent signal.

THE INCUBATOR

Figure 3:
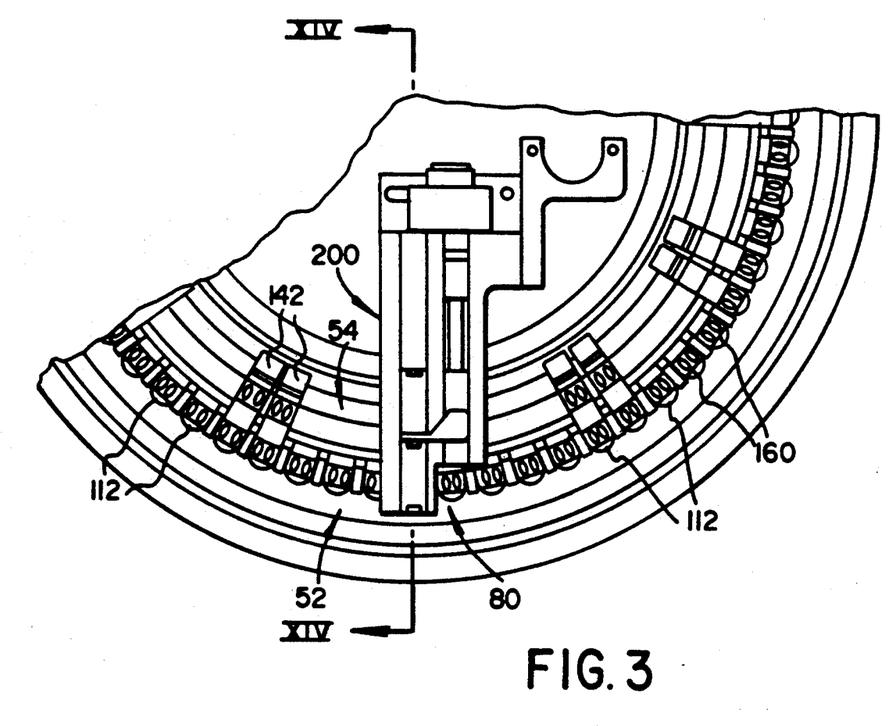
FIG. 3 is a fragmentary plan view of the incubator of FIG. 2 with the cover removed.

In accordance with the invention, incubator 50 comprises two concentrically mounted support rings 52, 54 for receiving and carrying cuvettes C (delivered preferably first to ring 52 by any pusher means 43), rotating means for independently rotating rings 52 and 54 about a common axis 55, moving means 200 (FIG. 3) discussed hereinafter, for moving a cuvette, arrow 56 of FIG. 2, from ring 52 to 54, processing stations around the rings, and heating means to incubate the contents of the cuvettes on rings 52 and 54. Rings 52 and 54 are shown only schematically in FIG. 2 in association with the related components. Rotating means for the rings preferably comprise gear teeth 62, 64 disposed on each of rings 52 and 54, respectively, to be driven by pinion gears 66 and 68.

As noted above, various processing stations are disposed around the circumference of rings 52 and 54, in addition to an entrance port 70 for cuvettes C. They are as follows, FIGS. 1 and 2: Station 72 is permanently disposed above ring 52 and is the place where the dispensing tip 37 of aspirator 20 (not shown in FIG. 2) descends to dispense sample into a cuvette in ring 52. First reagent addition station 74 is permanently disposed at least above ring 52 so that the permanent tip of aspirator 22 can dispense at least a first reagent into a cuvette in ring 52. Optionally, aspirator 22 can also be used to dispense a second reagent, namely a conjugate reagent, as well. Second reagent addition station 76, here for signal reagent, is disposed permanently above at least inner ring 54, to descend to dispense signal reagent into a cuvette in ring 54. Wash dispensing station 78 is disposed permanently above ring 54 for washing cuvettes using wash dispenser 30. Luminometer 32 is permanently disposed above ring 54 for reading chemiluminescence. Finally, transfer means 200 (FIGS. 3 and 14–16) is disposed at station 80 to transfer cuvettes from ring 52 to ring 54, FIG. 2, arrow 56, and then from ring 54 to a dump, arrow 82, or back to ring 52 temporarily. Although not shown, reagent addition stations 74 and 76 can be constructed to bridge both rings, if desired, so as to allow the respective transfer means to supply reagent to both rings, albeit in separate sequences.

The temperature control for rings 52 and 54 comprise any conventional heating mechanism, such as heater elements (not shown) disposed in a cover plate 90, shown in phantom, and in stationary support tracks, e.g., track 100 disposed below both the rings, described hereinafter. Cover plate 90 is apertured at the processing stations, such as entrance port 70, an access port 102 for station 74, and the others not shown in the rest of the cover plate needed for stations 76, 78 and luminometer 32. Additionally, cover plate 90 is removed at groove 104 at station to accommodate transfer means 200, shown hereinafter.

Figure 4:
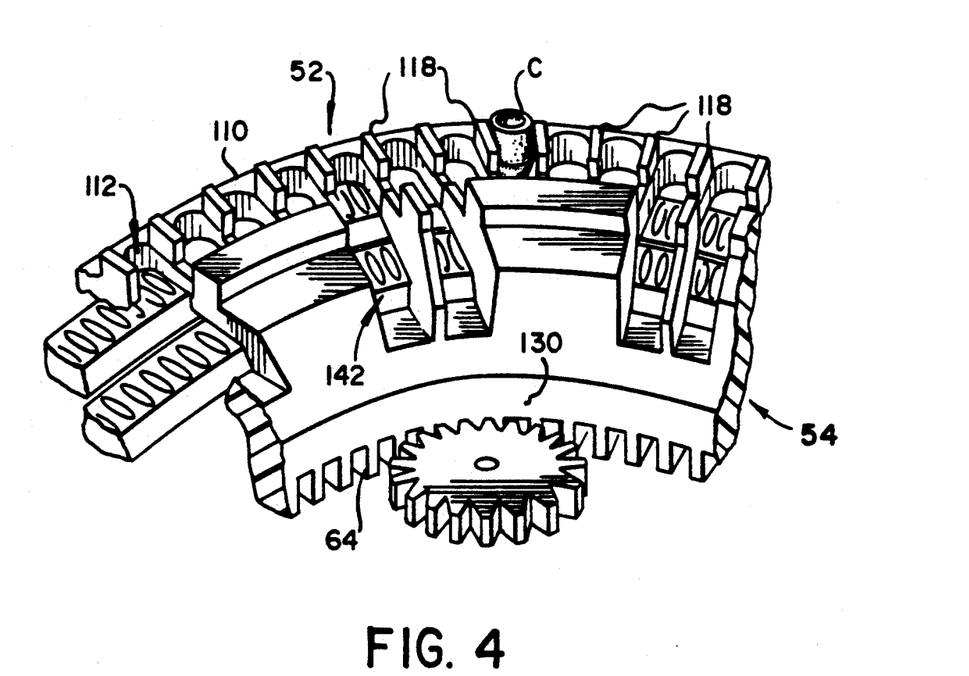
FIG. 4 is a fragmentary isometric view similar to that of FIG. 2, showing details of a segment of the incubator.
Figure 5:
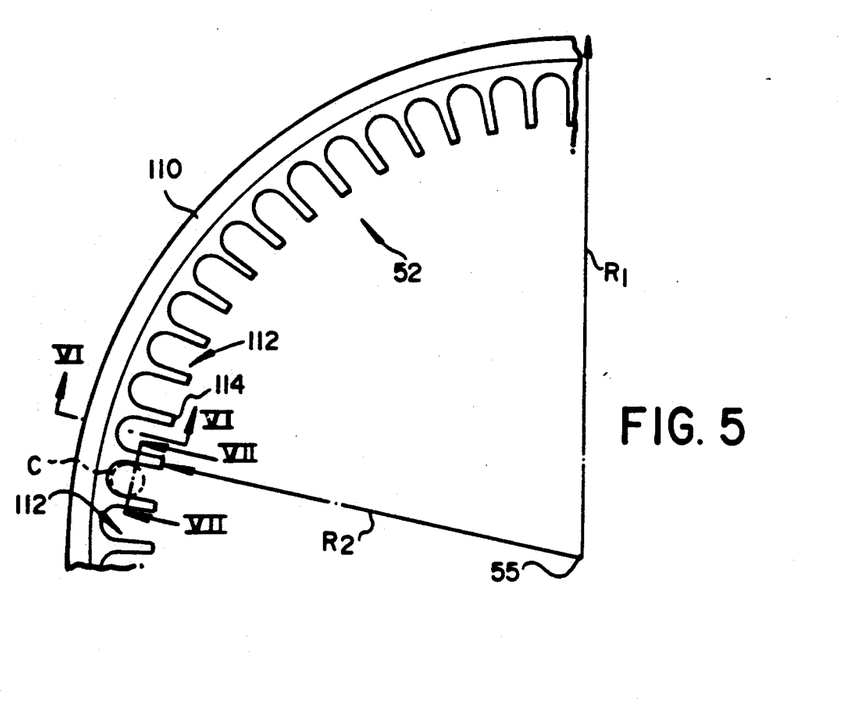
FIG. 5 is a fragmentary plan view of the outer ring of the incubator, showing one quadrant which repeats itself around the circumference of the ring.
Figure 6:
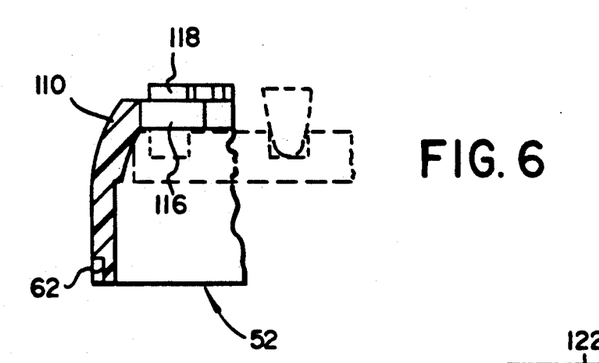
FIG. 6 is a section view taken generally along the line VI—VI of FIG. 5, the associated stationary track and a cuvette being shown in phantom.

Outer ring 52, FIGS. 3–6, preferably comprises an annulus defined principally by a continuous outer shoulder 110, FIGS. 4–6, having an outside radius $R_1$ extending from axis 55, FIG. 5. To define slots 112 for each cuvette, notches are formed in the annulus from the inside surface 114 of the annulus having an inside radius of curvature $R_2$. The notches are open towards axis 55, so that a cuvette C (in phantom) can be moved from outer ring 52 to the inner ring and back if necessary, without taking the cuvette out of the plane of the rings, the rings being co-planar as shown. Between each notch 112 there is a spoke fragment 116 shaped to support a cuvette C on top of ring 52, FIG. 7. Although spokes 116 can have a variety of cross-sectional shapes, preferred is one which is an upside-down T such that the top portion "t" of cuvette C is held between fixed shoulders 118 to prevent pivoting about point 120, arrow 122 (The support of the cuvettes is most clearly shown in FIG. 7). Shoulders 118 are particularly useful if track 100 is provided with optional ribs 160, as shown, as shoulders 118 then reduce the rocking motion 122 that would otherwise be induced.

As shown in FIG. 6, gear teeth 62 preferably depend from the bottom portion of ring 52.

Figure 8:
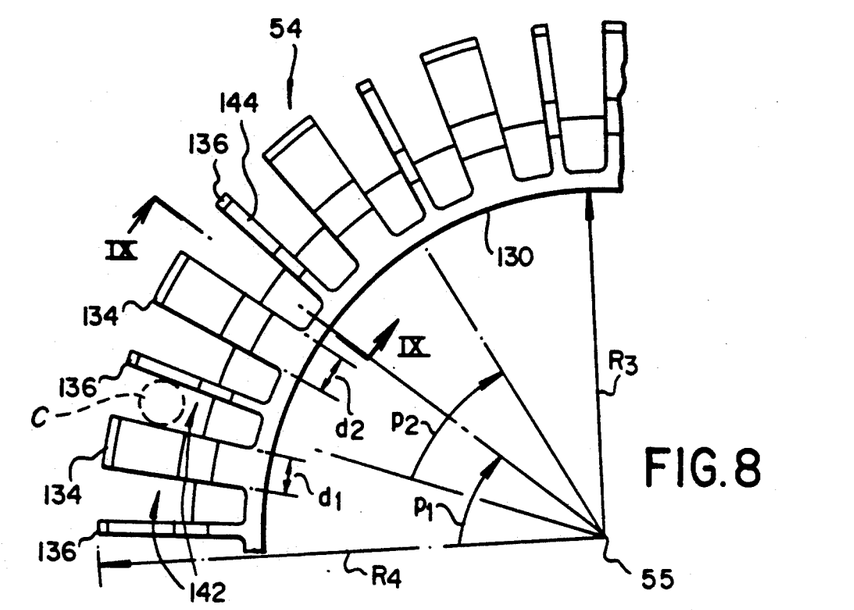
FIG. 8 is a fragmentary plan view of one quadrant of the inner ring, which quadrant repeats itself around the circumference of the ring.
Figure 9:
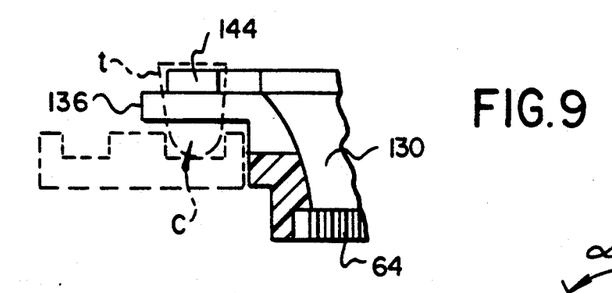
FIG. 9 is a section view taken along the line IX—IX of FIG. 8, the associated track and cuvette being shown in phantom.

Inner ring 54 comprises, FIGS. 4 and 8–9, a base annulus 130 extending completely around the circumference and having an inside radius of curvature $R_3$ measured from axis 55, FIG. 8. Mounted preferably on the inside portion of annulus 130 is a skirt with gear teeth 64, FIG. 9. Extending upward and outwardly away from annulus 130 at spaced intervals, with an outside radius $R_4$, FIG. 8, are wide flanges 134 and narrow flanges 136, spaced apart to define notches 142, each shaped to receive and carry a cuvette C (shown in phantom). Most preferably, notches 142 are in pairs with a narrow flange 136 dividing up each pair. The pitch $P_1$ between each of every other pair is controlled to match the angular spacing around the circumference of stations 76, 78 and 32. Pitch $P_2$ for the intermediate set of pairs equals pitch $P_1$, but the spacing $d_1$ and $d_2$ that positions each pair from its adjacent pair need not be equal.

Figure 7:
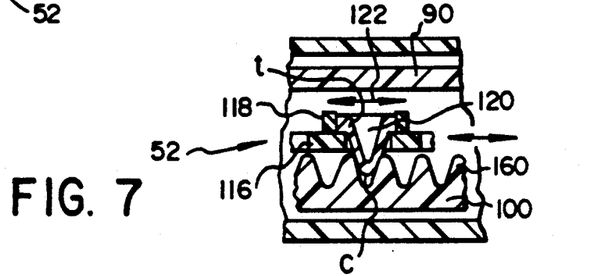
FIG. 7 is a fragmentary sectional view taken generally along the line VII—VII of FIG. 5, and showing a cuvette in solid lines.

Each flange 134 and 136 is shaped in cross-section as an upside down "T", similar to the spokes 116 of ring 52, FIG. 7, to provide a shoulder 144 to support upper portion "t" to the cuvette (in phantom).

Importantly, notches 142 differ from notches 112 of ring 52 in that they are open in both directions, away and towards axis 55, FIGS. 4 and 9. This is needed to allow a cuvette to be moved into ring 54 from ring 52, and then into the dump, arrow 82 of FIG. 1, that is inside annulus 130.

Each of rings 52 and 54 includes flag means (not shown) that allow either a "home" position, or each cuvette position, to be sensed by a conventional sensor.

Figure 10:
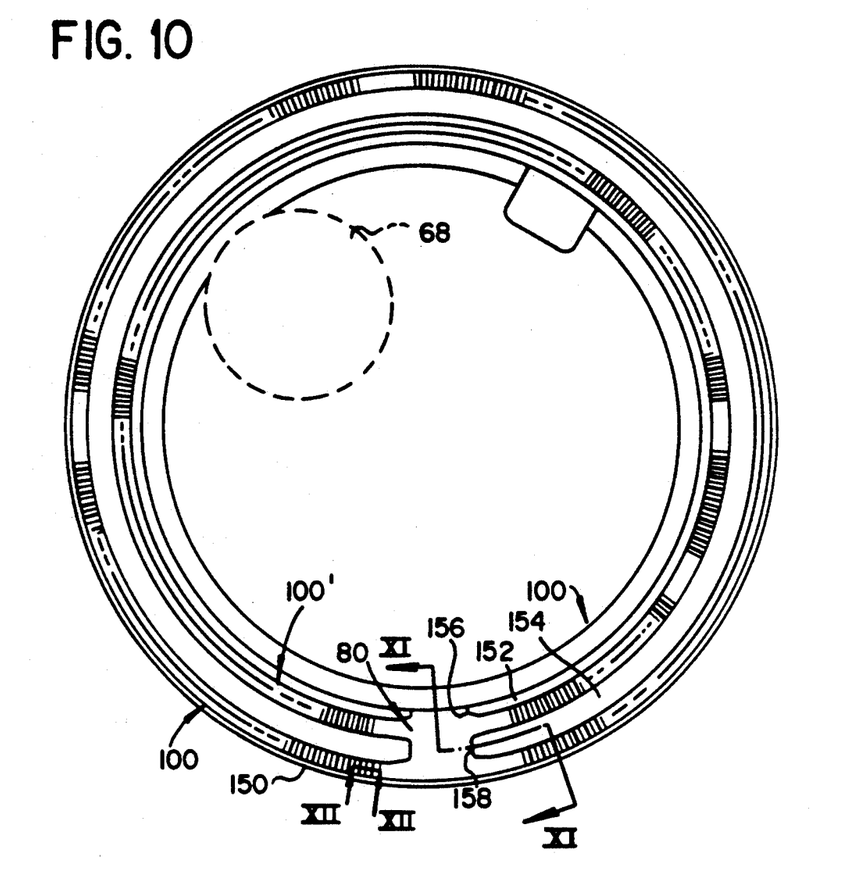
FIG. 10 is a plan view of a preferred form of the stationary track associated with the incubator.
Figure 11:
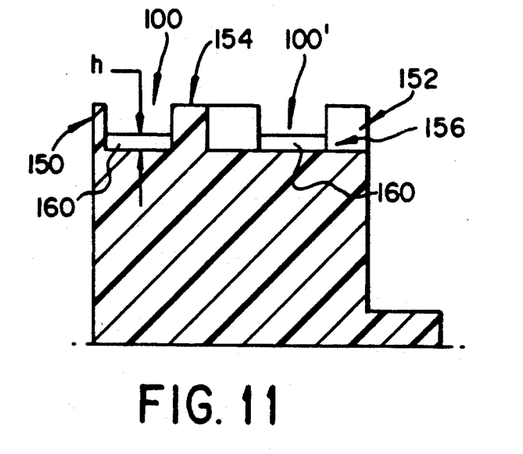
FIG. 11 is a section view taken generally along the line XI—XI of FIG. 10.
Figure 12:
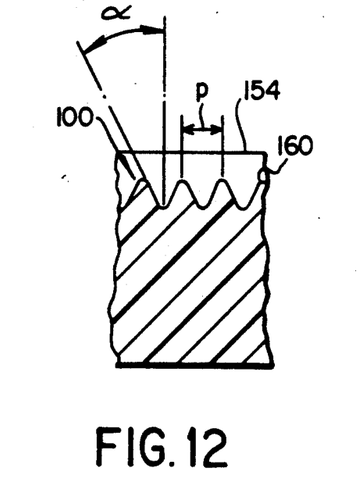
FIG. 12 is a section view taken generally along the line XII XII of FIG. 10.

Turning next to stationary tracks 100, 100′, FIGS. 11 and 12, these can have a variety of surface configurations. If cuvettes C are agitated while on rings 52 and 54 by some other mechanism, then the top surface of tracks 100 can be smooth, except for rails 150, 152 and 154, described hereinafter. The top surface of each track is provided with ribs 160, to cause cuvettes C to be agitated. More specifically, FIGS. 10 and 17, tracks 100 and 100′ are provided with an outside guide rail 150 that runs along outside of the path of cuvettes C carried by ring 52, FIG. 17. Track 100′ is provided with an inside guide rail 152 that runs along inside of the path of cuvettes C′ carried by ring 54, and a guide rail 154 is disposed between the aforesaid two tracks and hence between rings 52 and 54. Rails 150, 152 and 154 serve to retain the cuvettes from being inadvertently displaced sideways, towards or away from axis 55. However, FIG. 10, only guide rail 150 extends completely around the circumference of track 100. Guide rail 152 is continuous except for notch 156 at station 80, so that cuvettes C′, FIG. 16, can be dumped from ring 54. Guide rail 154 is the same as rail 152—it is continuous except for a notch 158 at station 80, to allow transfer of cuvettes from ring 52 to ring 54.

As noted above, tracks 100 and 100′ between paired rails 150, 152, and 154 can be smooth, but are preferably provided with ribs 160, as are more clearly shown in FIGS. 11 and 12. The pitch "p" and height "h" are adjusted to give agitation to the contents of cuvettes C and C′ to cause mixing but without spilling liquid from the cuvettes. The values of p and h depend on the rate of mixing that is desired, as well as the speed of transit over the ribs and the height of the cuvette. Further, pitch p can be different for each track, if the transit speed is different. As an example, for a transit speed of between about 20 cm/sec and about 60 cm/sec, and a cuvette height of about 12 mm, "h" can vary between about 0.6 mm and about 3.0 mm, and "p" can vary between about 1 mm and about 5.0 mm, with angle alpha, FIG. 12, being between about 40 degrees and about 50 degrees. Because of restraining shoulders 118 and 144, the cuvettes are induced to "bump" over the ribs, within the confines of cover plate 90, FIG. 17. That is, cover 90, FIGS. 7 and 17, assists in preventing the cuvettes from rising too far out of their notches.

Figure 13:
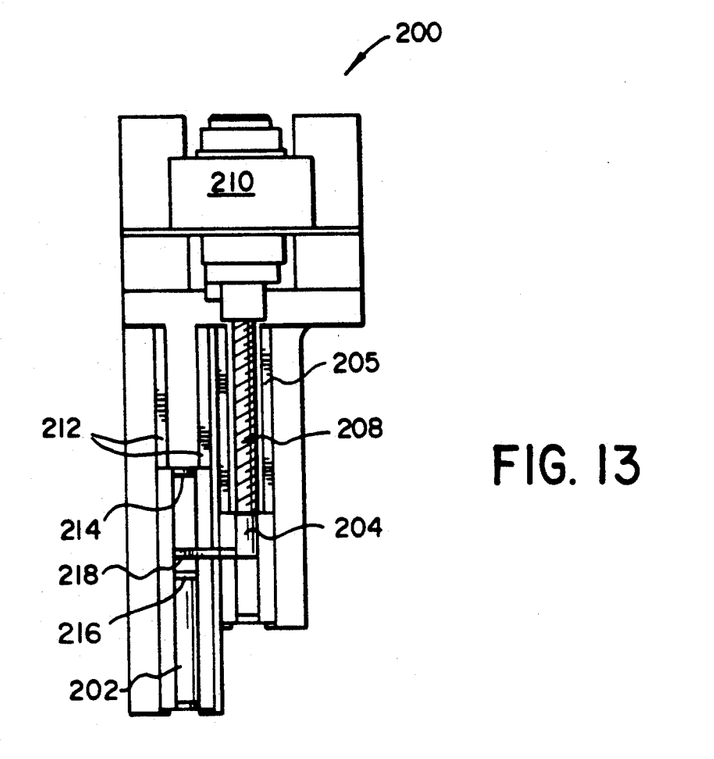
FIG. 13 is a plan view of just the transfer means 00 for moving a cuvette off the incubator rings.

Means are needed for moving cuvettes from ring 52 to ring 54, and then off ring 54 out to dump. To that end, at station 80 there is provided transfer means 200, FIGS. 13–16. Such means comprise preferably a push rod 202, 204 for each of the outer and inner rings 52 and 54, respectively, mounted for transverse, reciprocal movement above their respective rings. Each rod has a terminal lip 206, FIGS. 14–16, which depends down far enough to engage any cuvette that is aligned therewith when the rod is pulled towards axis 55. To reciprocate each rod, a drive can be provided for each. Preferably, however, only rod 204 is driven (along tracks 205, FIG. 13), by reason of the rod being internally threaded to engage a lead screw 208 driven by stepper motor 210. Rod 202, on the other hand, is a follower rod that is slidably and freely mounted on track 212, with tabs 214 and 216 rising therefrom, FIGS. 14–16, to be engaged by a collar 218 on rod 204 that encircles rod 202.

Figure 14:
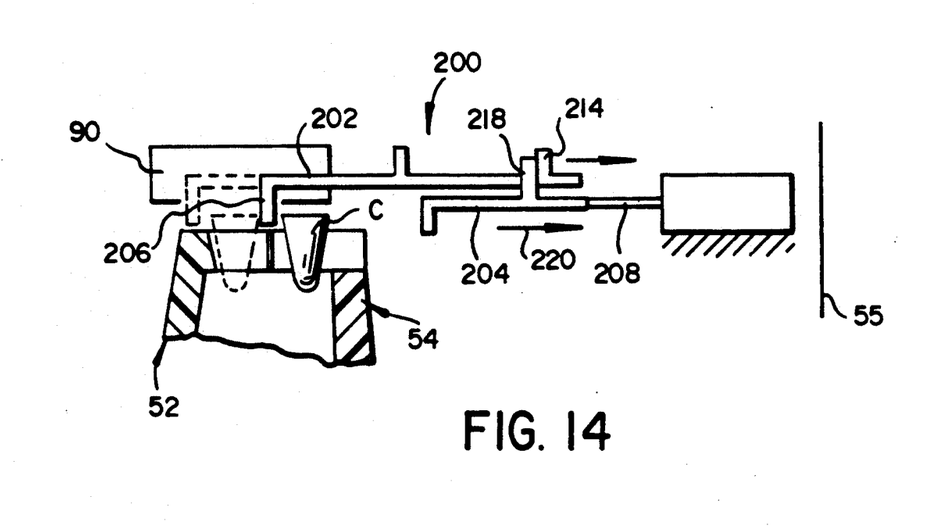
FIG. 14 is a partially schematic, fragmentary section view taken generally along the line XIV—XIV of FIG. 3.
Figure 15:
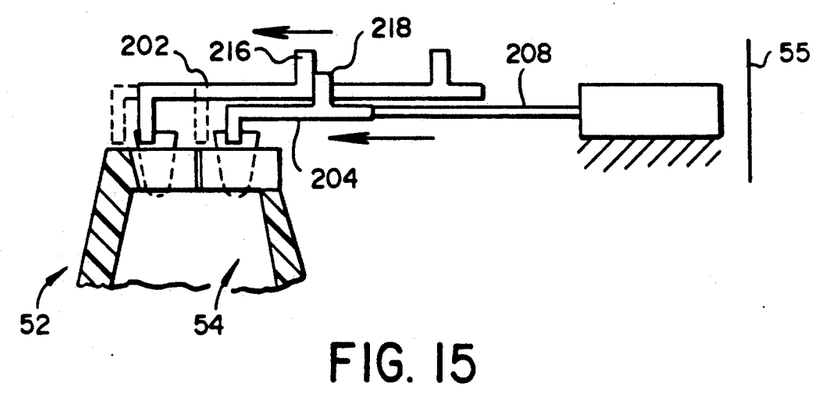
FIGS. 15-16 are fragmentary elevational views in section similar to FIG. 14, showing the shuttle mechanism as it moves the cuvettes from one ring to another and then out of the incubator.
Figure 16:
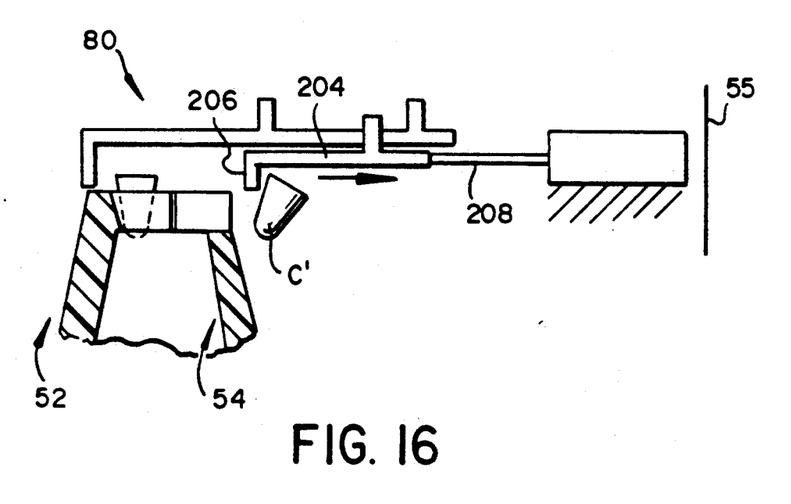

The operation of transfer means 200 will be readily apparent from the preceding. As shown in FIGS. 14–16, when a cuvette shown in phantom needs to be transferred at station 80 from ring 52 to ring 54, push rod 204 is drawn back, arrow 220, by lead screw 208, until collar 218 engages tab 214. This causes rod 202 to also traverse towards axis 55, from its phantom position, causing lip 206 thereof to move cuvette C to its solid position on ring 54. The next part of the cycle of movement, FIG. 15, is to move both rods to the outside of their respective rings, and this is done by advancing lead screw 208 and rod 204 away from axis 55 until collar 218 presses against tab 216 and pushes out rod 202 as well, from its solid position to that shown in phantom (between spaces occupied by cuvettes).

The last part of the cycle of movement is that used to transfer a cuvette C' from ring 54 to dump, FIG. 16, at station 80. Lead screw 208 simply withdraws enough to cause lip 206 of rod 204 to pull cuvette C' off ring 54.

It will be understood that one of the notches 142 is maintained empty of cuvettes to provide clearance for movement of lip 206 between rings.

Alternatively, in some assays the cuvette is transferred back to outer ring 52 for further reagent addition and incubation, before returning to ring 54 for washing and reading.

Figure 17:
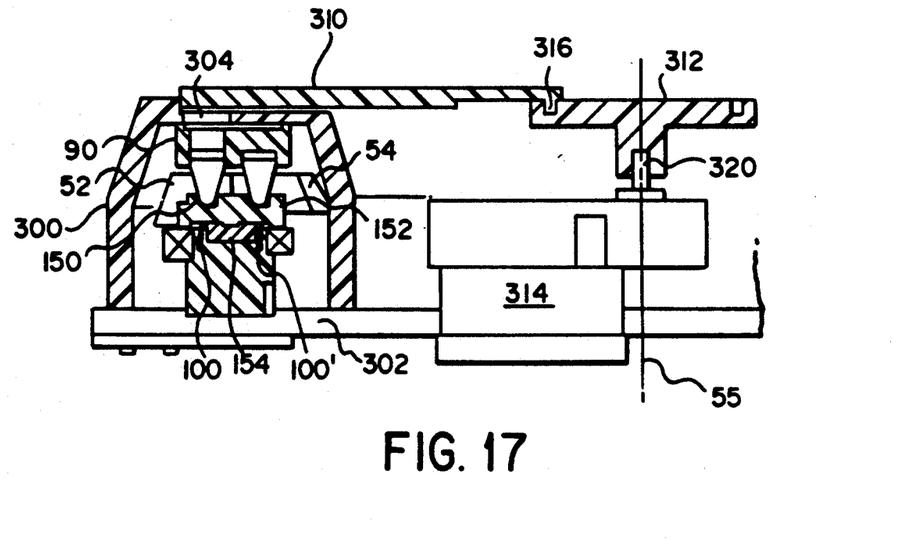
FIG. 17 is a section view taken generally along the lines XVII—XVII of FIG. 1.

In addition to heated cover 90 and stationary tracks 100, 100', additional insulative enclosures are preferably provided, FIG. 17, to retain the heat for incubation of incubator 50. That is, a housing 300 is mounted on a base 302 of an insulative material, with suitable apertures 304 positioned for access to the incubator. Those apertures are generally aligned with the apertures of cover 90, FIG. 2. Most preferably, apertures 304 are removably covered by doors 310, which can be operated by any suitable means, such as a cam 312 driven by motor 314 to engage cam followers 316 on the doors, as is more fully described and claimed in commonly owned U.S. application Ser. No. 887,976 filed on May 22, 1992 by J. J..Porte and entitled CAM-OPERATED DOORS FOR AN INCUBATOR. Most preferably, drive shaft 320 of motor 314 is on axis 55, FIG. 17.

The actual control of the temperature within incubator 50 is variable, depending on the reactions desired. Most preferably, the temperature of outer ring 52 is preferably kept within 0.5° C. of the desired temperature, e.g., of 37°, as most of the incubation occurs while on this ring. Inner ring 54, on the other hand, can be within 2° C. of the desired target temperature, but most preferably ±0.5° C.

The timing sequence for the operation of the incubator will of course depend upon a large variety of factors, including a) the angular position of each processing station about the rings of the incubator, and b) the chemistry of the immunoassays in question, as will be readily apparent.

Figure 18A:
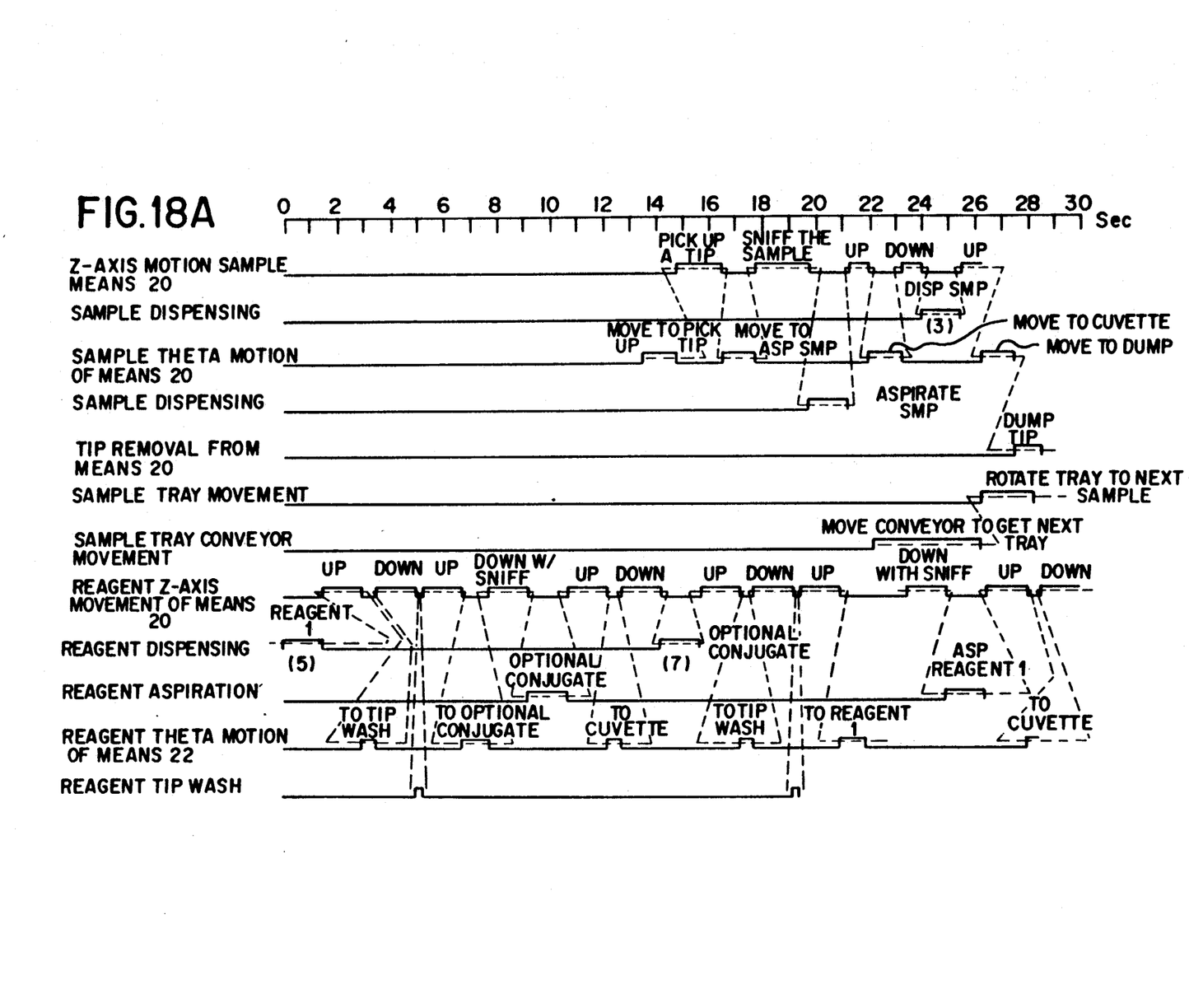
FIG. 18A-B are timing diagrams showing representative timing of the operations provided by the incubator of the invention.
Figure 18B:
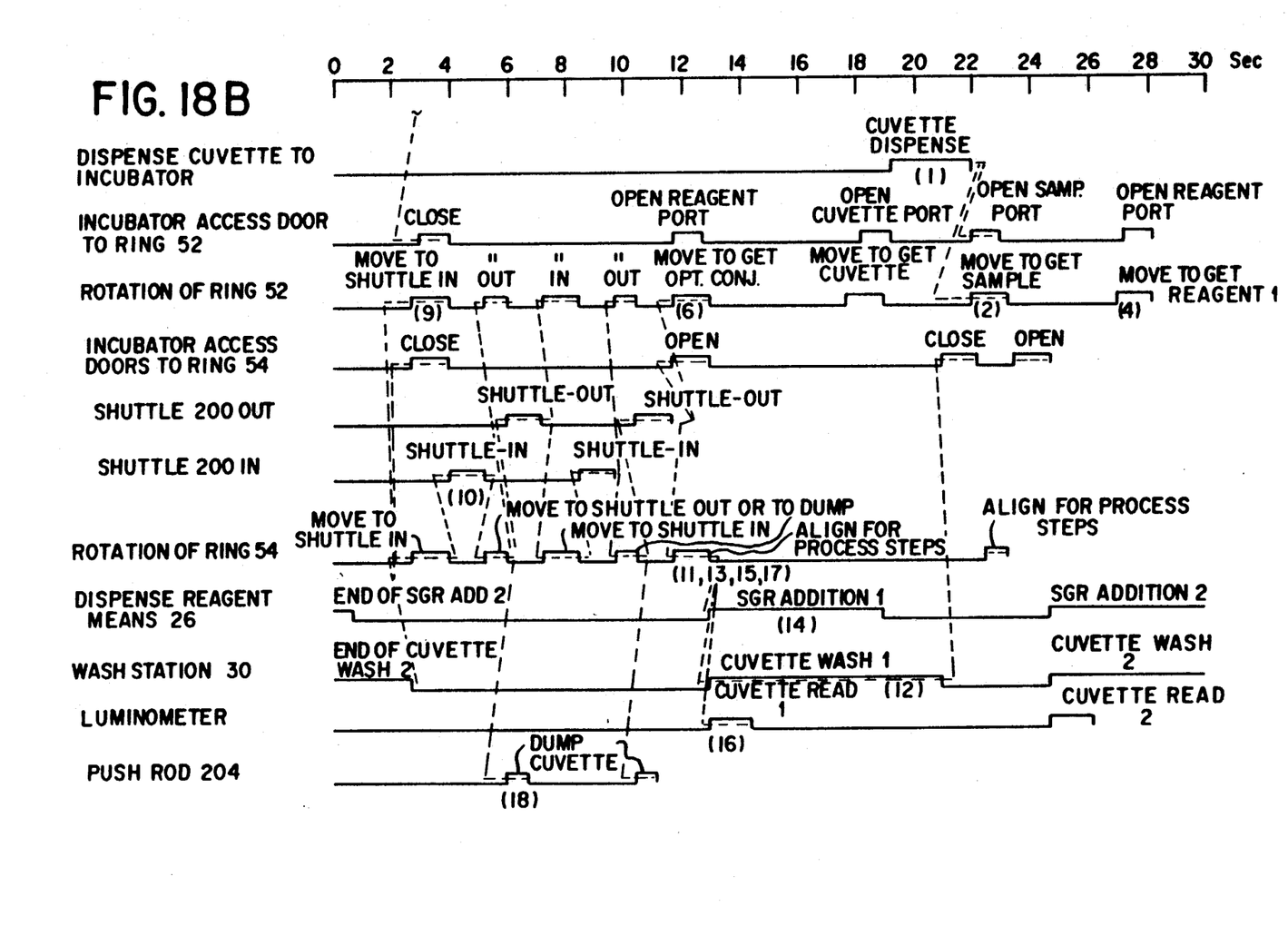

A representative timing diagram is given in FIG. 18A and B. In this diagram, it is assumed that reagent transfer means 22 goes to reagent supply station 16, FIG. 1, twice for two different reagents. The first 15 functions are defined as operations pertaining to outer ring 52, whereas the remainder are for inner ring 54.

Considering the overall operation of the incubator, it proceeds as follows, under the control of conventional computing means (not shown). ("Step" numerals appear in parantheses in FIGS. 18A and B, and "SGR" is an abbreviation for "signal reagent".)

Step 1: a cuvette C is dropped into a notch in outer ring 52.

Step 2: ring 52 is rotated to move that cuvette into position at station 72 (FIG. 2) to receive a sample liquid.

Step 3: sample is dispensed at station 72.

Step 4: ring 52 is rotated to move the cuvette to reagent addition station 74 (FIG. 2).

Step 5: reagent is dispensed at station 74 using transfer means 22.

Step 5': rotate ring 52 to allow other operations on other cuvettes, while incubating and agitating this cuvette.

Step 6: rotate ring 52 to move it back to station 74 for optional conjugate reagent addition.

Step 7: dispense second reagent, if needed.

Step 8 (not labeled on FIG. 18): incubate and agitate for a minimum of 15 minutes.

Step 9: rotate ring 52 (and ring 54) to place cuvette at station 80.

Step 10: activate transfer means 200 to move cuvette from ring 52 to ring 54.

Step 11: align cuvette on ring 54 at station 78 for washing of the cuvette.

Step 12: wash cuvette at station 78.

Step 13: repeat alignment step 11 until cuvette is at station 76.

Step 14: dispense signal reagent at station 76.

Step 15: repeat alignment step 11 until cuvette is at read station 32.

Step 16: read cuvette with the luminometer.

Step 17: repeat step 11 until cuvette is at station 80.

Step 18: activate push rod 204 to dump the cuvette.

Figure 19:
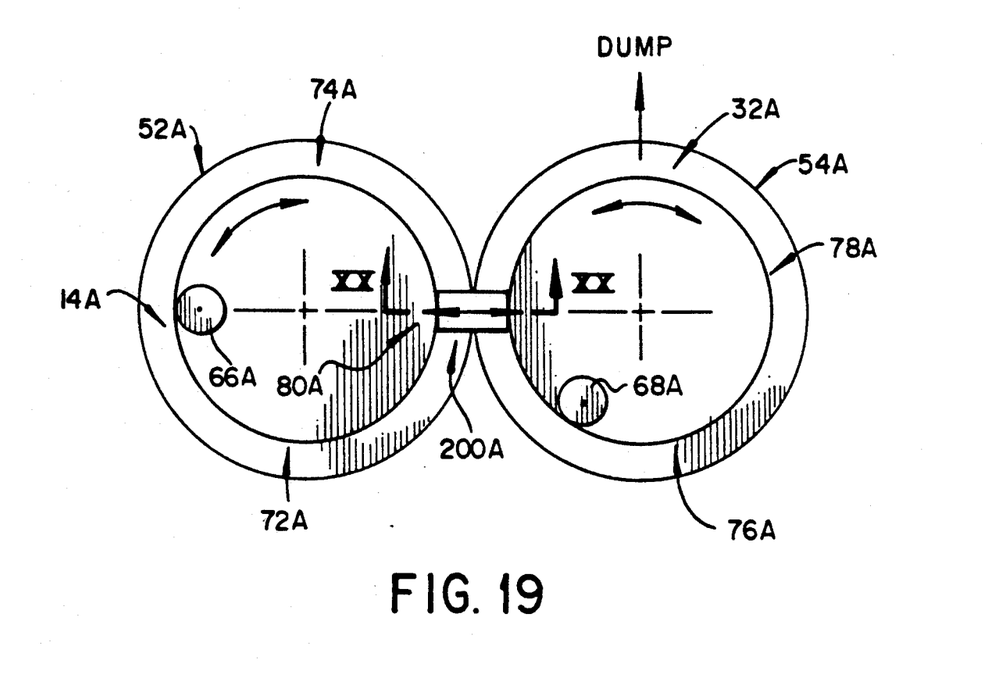
FIG. 19 is a schematic plan view of an alternate form of the incubator, wherein the rings are not concentric.
Figure 20:
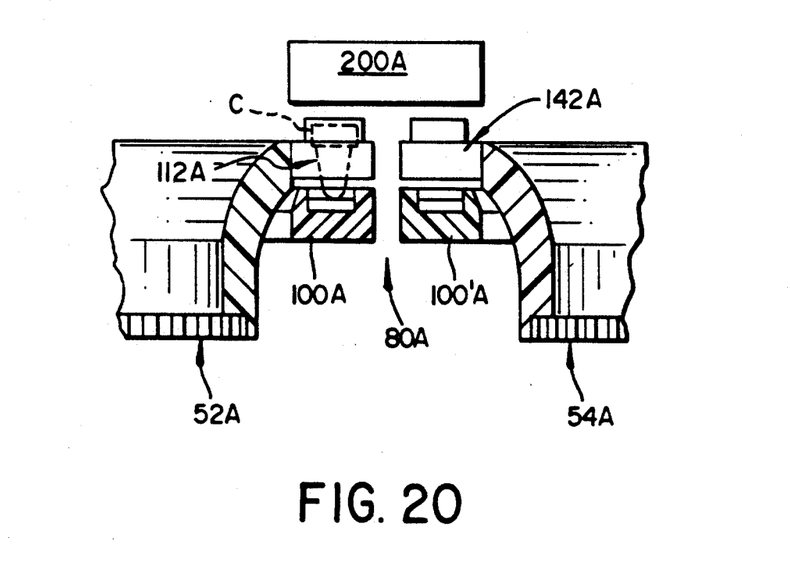
FIG. 20 is a fragmentary section view taken generally along the ling XX—XX of FIG. 19.

As noted heretofore, the plural rings need not be concentrically mounted—indeed they need not be one within the other, FIGS. 19–20. Parts similar to those previously described bear the same reference numeral to which the distinguishing suffix "A" is appended. Thus, rings 52A and 54A can be side-by-side, separately rotated about separate axes by gears 66A and 68A, FIG. 19. The various stations 14A, 72A, 74A are disposed adjacent ring 52A as before, whereas stations 32A, 76A and 78A are disposed adjacent ring 54A as before. Each ring 52A and 54A, FIG. 20, is preferably notched at 112A and 142A, respectively, so that the notches open outwardly only, to allow transfer at station 80A of a cuvette "C", between rings using transfer means 200A. Fixed track 100A and 100'A are separate annulii that surround only their respective rings.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. An incubator in an analyzer for detecting an analyte, the incubator comprising plural support rings each in a common plane, for carrying between processing stations of said incubator, reaction cuvettes held at positions that are open at least radially toward an adjacent one of said rings;

means for rotating each of said support rings independently, between said stations;

means for moving at a transfer location, a reaction cuvette from one support ring to the other without taking the moving cuvette out of the plane of said rings, or off the rings, at an appropriate stage within the incubator;

processing stations adjacent to said rings to provide separately means for the functions of sample addition, first liquid reagent addition, second liquid reagent addition, cuvette washing, optional third liquid reagent addition, and detection of light emitted from the reaction cuvettes, at least said first liquid regent addition station being permanently disposed adjacent to at least one of said rings, while at least said second liquid reagent addition station is permanently disposed adjacent to at least another of said rings;

and temperature control means adjacent to both of said rings, so that a higher number of detected analytes per hour is achieved by separating and distributing the incubating functions onto more than one support ring, than is achieved using only one such ring.

2. An incubator as defined in claim 1, wherein said plural rings are concentrically mounted about an axis, and wherein said one support ring is the outer of said rings and said other support ring is the inner of said rings.

3. An incubator as defined in claim 2, wherein each of said rings is rotated above a stationary track having on at least potions thereof, opposing guide rails to retain cuvettes under a respective ring from sideways displacement towards or away from said axis.

4. An incubator as defined in claim 3, wherein one of said guide rails is disposed between two of said rings, and wherein said one rail is notched at said transfer location so as to present no barrier to sideways movement of a cuvette from one ring to the other.

5. An incubator as defined in claim 4, wherein another of said opposing guide rails is disposed around the inside of the innermost ring, said another opposing guide rail being notched sufficiently to allow a cuvette to be removed from the track of said inside ring inwardly towards said common axis.

6. An incubator as defined in claim 4, wherein said notch of said another opposing guide rail is located at said transfer location.

7. An incubator as defined in claim 3, wherein one of said guide rails is disposed around the inside of the innermost ring, said inside guide rail being notched sufficiently to allow a cuvette to be removed from the track of said inside ring inwardly towards said common axis.

8. An incubator as defined in claim 3, wherein said outer ring includes an outer shoulder extending the entire circumference of said outer ring at a radius beyond the track of said ring, of a height sufficient to keep a cuvette from falling away from said ring and its track, said outer ring having notches on an inner portion extending opposite to said outer shoulder at each position, so a cuvette in any of said positions can be transferred inward from said outermost ring but not outward.

9. An incubator as defined in claim 8, wherein said inner ring comprises a bas annulus, a skirt depending from said base annulus and having a ring gear in said skirt for engaging a gear of said rotating means, and at intervals spaced along the circumference of said base annulus, flanges extending radially above and beyond said annulus at a height effective to hold a cuvette between said flanges.

10. An incubator as defined in claim 3, wherein said inner ring comprises a base annulus, a skirt depending from said base annulus and having a ring gear in said skirt for engaging a gear of said rotating means, and at intervals spaced along the circumference of said base annulus, flanges extending radially above and beyond said annulus at a height effective to hold a cuvette between said flanges.

11. An incubator as defined in claim 2, wherein said cuvette-moving means comprises a push rod for each of said rings, mounted for reciprocation above its respective ring, and means for moving said rod transversely across their respective rings at a height that catches a cuvette in the respective ring and moves it from that ring.

12. An incubator as defined in claim 11, wherein said push rod for said inner ring is connected to drive means, and wherein said push rod for said outer ring comprises a follower rod with means for engaging said inner ring push rod at the extremities of movement of said inner ring push rod.

13. An incubator in an analyzer for detecting an analyte, the incubator comprising a stationary guide track, plural support rings above said track for carrying between processing stations of said incubator, reaction cuvettes held at defined positions, said positions comprising openings in said rings sized to receive and to hold said reaction cuvettes;

means for rotating each of said support rings independently, between said stations;

means for moving a reaction cuvette from one support ring to the other at a transfer location, or off the rings, at an appropriate stage within the incubator, said moving means including in at least one of said rings a passageway notch extending from each of said cuvette-holding openings to a dump position on said ring, said notch and said stationary guide track being constructed to allow a cuvette to be dumped at said dump position;

processing stations adjacent to said rings to provide separately means for the functions of sample addition, first liquid reagent addition, second liquid reagent addition, cuvette washing, optional third liquid reagent addition, and detection of light emitted from the reaction cuvettes, at least said first liquid reagent addition station being permanently disposed adjacent to at least one of said rings, while at least said second liquid reagent addition station is permanently disposed adjacent to at least another of said rings;

and temperature control means adjacent to both of said rings, so that a higher number of detected analytes per hour is achieved by separating and distributing the incubating functions onto more than one support ring, than is achieved using only one such ring.

* * * * *

UNITED STATES PATENT AND TRADEMARK OFFICE
CERTIFICATE OF CORRECTION

PATENT NO. : 5,244,633

DATED : September 14, 1993

INVENTOR(S) : Raymond F. Jakubowicz et al

It is certified that error appears in the above-indentified patent and that said Letters Patent is hereby corrected as shown below:

Column 3, line 19, delete "00" and substitute therefor --200--

Column 5, line 25, after "station", insert --80--

Column 6, line 4, delete "to" and substitute therefor --of--

Signed and Sealed this

Twenty-ninth Day of March, 1994

Attest:

BRUCE LEHMAN

Attesting Officer

Commissioner of Patents and Trademarks